(12) United States Patent
Reynolds et al.

(10) Patent No.: US 6,475,751 B2
(45) Date of Patent: Nov. 5, 2002

(54) SCINTILLATION PROXIMITY ASSAY FOR TYPE II FATTY ACID BIOSYNTHETIC ENZYMES

(75) Inventors: Kevin A. Reynolds, Chesterfield, VA (US); Xin He, Richmond, VA (US)

(73) Assignee: Virginia Commonwealth University, Richmond, VA (US)

(*) Notice: Subject to any disclaimer, the term of this patent is extended or adjusted under 35 U.S.C. 154(b) by 15 days.

(21) Appl. No.: 09/754,076

(22) Filed: Jan. 5, 2001

(65) Prior Publication Data

US 2001/0031477 A1 Oct. 18, 2001

Related U.S. Application Data

(60) Provisional application No. 60/174,806, filed on Jan. 7, 2000.

(51) Int. Cl.[7] .............................. C12Q 1/48; C12Q 1/00; G01N 33/53
(52) U.S. Cl. ........................ 435/15; 435/7.5; 435/7.1; 435/975; 435/968; 435/4
(58) Field of Search ........................... 435/15, 7.5, 7.1, 435/975, 968, 4

(56) References Cited

U.S. PATENT DOCUMENTS 6,168,797 B1 * 1/2001 Biswas et al. ............ 424/244.1

FOREIGN PATENT DOCUMENTS

WO 200151925 * 7/2001

* cited by examiner

*Primary Examiner*—Louise N. Leary
(74) *Attorney, Agent, or Firm*—Whitham, Curtis & Christofferson, P.C.

(57) ABSTRACT

The present invention provides scintillation proximity assays (SPAs) for measuring the activity of enzymes involved in type II fatty acid biosynthesis. Enzymes which can be assayed in this manner include KASI, KASII, KAS III and MAT. The present invention also provides methods of assaying for ketoacyl synthase activity, malonyl transferase activity, and acyl transferase activity in enzymes using the SPA format. Because the SPA format allows the direct detection of a radiolabeled product, these assay methods are appropriate for use in high throughput screening techniques. The present invention also provides methods for assessing a compound's ability to modulate the activity of a type II fatty acid biosynthetic enzyme.

68 Claims, 8 Drawing Sheets

SCINTILLATION PROXIMITY ASSAY FOR TYPE II FATTY ACID BIOSYNTHETIC ENZYMES

This application claims the benefit of Provisional application Ser. No. 60/174,806, filed Jan. 7, 2000.

This invention was made using funds from the National Institute for Allergy and Infectious Diseases having a grant number 520757 A1 44772. The government may have certain rights in this invention.

FIELD OF THE INVENTION

This invention pertains generally to biological assays of components of a fatty acid synthase, and more particularly, to the use of scintillation proximity assays suitable for detecting and measuring activities such as that of β-ketoacyl-acyl carrier protein synthase III.

BACKGROUND OF THE INVENTION

The pathway for the biosynthesis of saturated fatty acids is very similar in prokaryotes and eukaryotes. However, while the chemical reactions may not vary, the organization of the biosynthetic apparatus is very different. Vertebrates and yeast possess type I fatty acid synthases (FASs) in which all of the enzymatic activities of the fatty acid biosynthetic pathway are encoded on one or two polypeptide chains, respectively, and an acyl carrier protein (ACP) is an integral part of the complex. In contrast, in most bacterial and plant type II FASs, each of the reactions is catalyzed by distinct monofunctional enzymes and the ACP is a discrete protein. Mycobacteria are unique in that they possess both type I and II FASs; the former is involved in basic fatty acid biosynthesis whereas the latter is involved in synthesis of complex cell envelope lipids such as mycolic acids.

The fatty acid biosynthetic process is divided into three phases: initiation, elongation and termination. The elongation phase is cyclical, in that acyl thioester (typically attached to an acyl carrier protein) is repeatedly elongated two carbons at a time using malonyl CoA as the 2-carbon "extender" unit.

In type II fatty acid biosynthesis (refer to FIG. 1) the first elongation step or initiation step is the condensation of malonyl-ACP (MACP) with an acyl-CoA which is catalyzed by β-ketoacyl-acyl carrier protein synthase III (KAS III or FabH, see definitions). The product of this reaction is β-ketoacyl ACP which then enters the reduction component of the cycle by undergoing ketoester reduction by NADPH-dependent β-ketoacyl-ACP reductase (FabG, "KR" in FIG. 1). Subsequent dehydration by β-hydroxyacyl-ACP dehydrase (either FabA or FabZ, represented by "DH" in FIG. 1) leads to trans-2-enoyl-ACP which is in turn converted to acyl-ACP by NADH-dependent enoyl-ACP reductase (FabI, "ER" in FIG. 1). Synthases KAS I and KAS II (also known as FabB and FabF, see definitions) then catalyze a 2-carbon elongation of acyl-ACP via condensation with MACP, followed by ketoester reduction, dehydration, and enoyl reduction as described above. Further rounds of this cycle, adding two carbon atoms per cycle, eventually lead to production of a fatty acid of the desired length, whereupon the cycle is stopped largely due to feedback inhibition of KASIII (Heath, et al, (1996), *J.Biol.Chem.* 271, 1833–1836). KASIII is therefore a major biosynthetic enzyme which is also a key regulatory point in the overall biosynthetic pathway (Heath, R. J. and Rock, C. O. 1996. *J.Biol.Chem.* 271, 1833–1836; Heath, R. J. and Rock, C. O. 1996. *J.Biol.Chem.* 271, 10996–11000). KASIII from different organisms exhibit different acyl CoA specificity, which appears to dictate the type of fatty acid product made. Thus, *E. coli* makes a mixture of odd and even-number straight chain fatty acids and its KASIII reacts preferentially with acetyl CoA and propionyl CoA (Heath and Rock, 1996. *J.Biol.Chem.* 271, 10996–11000). *Streptomyces glauecescens* and *Bacillus subtilis* make both branched and straight-chain fatty acids. The KASIII from these organisms have been shown to have a more relaxed substrate specificity, reacting with substrates such as isobutyryl CoA as well acetyl CoA and propionyl CoA (Choi, K. H., Heath, R. J. and Rock, C. O. 2000. β-ketoacyl-acyl carrier protein synthase III (FabH) is a determining factor in branched-chain fatty acid biosynthesis. *J Bacteriol* 182: 365–70; Han, L., Lobo, S. and Reynolds, K. A. 1998. Characterization of 3-ketoacyl acyl carrier protein synthase III from *Streptomyces glaucescens*: Its role in the initiation of fatty acid biosynthesis. *J Bacteriol* 180: 4481–4486). The KASIII of Mycobacterium tuberculosis on the other hand appears to have a substrate preference for long chain acyl CoA substrates and appears to be responsible for initiation of meromycolate fatty acid biosynthesis (Choi, K. H., Kremer, L., Besra, G. S., and Rock, C. O. 2000. *J. Biol. Chem.*)

The enzymes involved in type II fatty acid biosynthesis represent attractive targets for modulation of fatty acid synthesis in prokaryotes and plants. Substances that modulate type II fatty acid synthesis could potentially function as therapeutic agents (for example, as antibiotics), or as herbicides. Typically, the screening of potential enzymic effectors is carried out via high throughput screening (HTS) techniques. However, the currently available assay procedures for type II FAS enzymes are inadequate for HTS. For example, the traditional measurement of KASIII activity is a coupled enzyme trichloroacetic acid (TCA) precipitation assay (Han, L. et al. 1998 *J.Bacteriol.* 180, 4481–4486). In this assay, malonyl CoA-ACP transacylase (FabD, "MAT" in FIG. 1) is utilized to convert malonyl-CoA to malonyl-ACP. KAS III then catalyzes the condensation of malonyl-ACP with acetyl-CoA which has been radiolabeled, resulting in the production of the radiolabeled product 3-ketoacyl-ACP. An acid precipitation step is then used to physically separate the radioactive 3-ketoacyl-ACP product from the radiolabeled acetyl-CoA substrate. In addition to the precipitation step, an acid-washing step is also required to remove any residual radiolabeled acetyl-CoA from the precipitate. Only after these steps are completed can the radiolabeled, precipitated product be quantitated by scintillation counting.

A variation of this assay method involves binding the 3-ketoacyl ACP product to filter paper disks (such as Whatmann 3MM). These disks are then washed with three changes of ice cold tricchloracteric acid and the filters dried and counted using scintillation cocktail (Choi, Heath and Rock, 2000. *J Bacteriol.* 182, 365–370). Finally, a gel electrophoresis method has been described. This involves the use of radiolabeled malonyl CoA which is converted in the assay to malonyl ACP by the action of FabD. KASIII then catalyzes the formation of a radiolabeled ketoacyl ACP product using this malonyl ACP and a non-radioactive acyl CoA substrate. The radiolabeled product to reduced to the corresponding 3-hydroxyacyl ACP product by the action of FabG and NADPH and is then resolved from the other components of the assay by use of a polyacrylamide gel. Product quantitation is then obtained by exposure of the gel to a PhosphoImager screen (Choi, Heath and Rock, 2000. *J Bacteriol.* 182, 365–370).

Obviously, such multistep assay procedures are ill suited for high throughput screening methods. It would be highly desirable to have available a faster and more direct assay for the activities of the enzymes involved in type II fatty acid biosynthesis in order to screen libraries of their potential effectors at an acceptable rate and in a cost-effective manner.

SUMMARY OF THE INVENTION

The bacterial fatty acid biosynthesis pathway is a selective target for the development of novel antibiotics for treating infectious disease, (as shown in U.S. Pat. No. 5,614,551 which is incorporated herein by this reference). This selectivity is based both on the significant differences in the fatty acid synthases (FASs) of prokaryotes and eukaryotes and on their relative physiological importance. In higher organisms such as mammals, a multifunctional enzyme complex Type I fatty acid synthase (FAS) in which all of the enzymatic activities are encoded on one or two polypeptide chains, catalyzes the biosynthetic pathway. In humans, this pathway under most conditions is down-regulated due to exogenous dietary lipid intake. In contrast, fatty acid biosynthesis in bacteria appears to be an essential process catalyzed by a set of dissociable enzymes known collectively as a Type II FAS. The natural product thiolactomycin, a thiolactone antibiotic with in vitro and in vivo activity against a number of pathogenic bacteria, selectively inhibits type II, but not type I condensation reactions.

KASIII of Type II FASs has an important regulatory role and catalyzes the first step of fatty acid biosynthesis. This enzyme catalyzes the condensation of malonyl-ACP and acetyl CoA to generate 3-ketoacyl-ACP. Successive elongation steps in the Type II FAS use acyl ACP derivatives as acyl primers (rather than acyl CoA) and are catalyzed by separate 3-ketoacyl-ACP synthases. This pivotal role, the widespread conservation of KASIII among bacteria, and the fact that no mutants totally lacking KASIII activity have been described to date, suggests that this enzyme plays a essential role in bacterial growth. KASIII, therefore represents a promising target for novel antibiotics. Such antibiotics may be effective against bacteria which have become resistant to antibiotics interfering with other essential processes, such as cell-wall biosynthesis. With the exception of thiolactomycin, there are no antibiotics described which specifically target KASIII or other type II ketoacyl synthases. An appropriate assay suitable for high-throughput screening would facilitate the discovery of new KASIII modulators.

A new method of evaluating enzymatic activity in the bacterial type II fatty acid biosynthetic pathway is herein proposed as a solution to the problems outlined above. In a preferred embodiment of the method, in accordance with the present invention, a method to assay enzymatic activity of components of a type II FAS is described in which a reaction mixture is formed by combining a type II fatty acid biosynthetic enzyme, a substrate (ACP or MACP) which has been tagged with a ligand and a radiolabeled acyl or malonyl thioester. The reaction mixture is exposed to a Scintillation Proximity Assay (SPA) support system. The SPA system comprises trapped scintillant and a receptor for the ligand. A level of scintillation which correlates with a level of enzyme activity is measured. The type II fatty acid biosynthetic enzymes that may be assayed by this method include KASI, KASII, KASIII and MAT. The ligand may be biotin and the receptor may be avidin or streptavidin. The thioester may be CoA or ACP, although other thioesters such as those made by N-acetylcysteamine could also be used. The acyl group can vary in much the same way as the acyl thioester specificity of different KAS isozymes does. The APS support system may comprise a bead impregnated with scintillant.

The present invention further provides a method for assessing a compound's ability to modulate the enzymatic activity of a type II fatty acid biosynthetic enzyme. In the method, a test reaction mixture is formed by combining a type II fatty acid biosynthetic enzyme, a substrate (ACP or MACP) which has been tagged with a ligand and a radiolabeled thioester, and the compound. A control reaction mixture is formed by combining the same components without the compound. Both reaction mixtures are exposed to a Scintillation Proximity Assay (SPA) support system. The SPA system comprises trapped scintillant and a receptor for the ligand. Levels of scintillation which correlates with a level of enzyme activity are measured in both mixtures and the difference between the two levels is determined. The difference is correlated with the ability of the compound to modulate the enzymatic activity of the enzyme. The type II fatty acid biosynthetic enzymes that may be assayed by this method include KASI, KASII, KASIII and MAT. The ligand may be biotin and the receptor may be avidin or streptavidin. The radiolabeled thioester may be malonyl CoA, an acyl CoA, or acyl ACP. The SPA support system may comprise a bead impregnated with scintillant.

The present invention also provides new compositions of matter: biotinylated acyl carrier protein and biotinylated malonyl acyl carrier protein.

The present invention also provides a kit for assaying the enzymatic activity of a type II fatty acid biosynthetic enzyme. The kit includes ACP or MACP which has been tagged with a ligand, a radiolabeled acyl or malonyl thioester, and an SPA support system. Optionally, the kit may also include a type II fatty acid biosynthetic enzyme.

A test sample comprising a target enzyme is contactable with a test compound under suitable conditions that allow the components to interact. A radiolabeled acyl or malonyl thioester substrate and an acyl or malonylacyl carrier protein are added to the components and the enzymatic activity of the target enzyme in the test sample is compared to the enzymatic activity of the target enzyme in a sample not contacted with said test compound, wherein the difference in enzymatic activity in the test sample is indicative of the effect of said test compound on said target enzyme.

In the furtherance of this and other objectives, an assay is provided which is suitable for evaluating enzymatic activity in the bacterial type II fatty acid biosynthetic pathway, said method comprising: (a) contacting a test sample comprising a target enzyme with a test compound under suitable conditions that allow the components to interact; (b) adding to the components a radiolabeled acyl or malonyl thioester substrate and either an acyl carrier protein or malonyl acyl carrier protein; and (c) comparing the enzymatic activity of the target enzyme in the test sample to the enzymatic activity of the target enzyme in a sample not contacted with said test compound, wherein the difference in enzymatic activity in the test sample is indicative of the effect of said test compound on said target enzyme.

A principle object, in accordance with an exemplary embodiment of the present invention, is to provide a screening assay for KAS isozyme inhibitors. In the furtherance of this and other objectives, a rapid assay is provided for measuring the activity of compounds that inhibit KAS from a type II fatty acid synthase comprising, mixing the following components in solution: a test compound, KAS, radiolabeled acyl thioester substrate, a tagged malonyl acyl carrier protein to tagged acyl carrier protein and a product capture element. In particular, a rapid assay is provided for measuring the activity of compounds that affect the activity of β-ketoacyl-ACP Synthase III (KASIII) comprising, mixing the following components in solution: (a) KASIII; (b) the compound, whose effect on KASIII is to be measured; (c) conjugate comprising, a high affinity moiety and an acyl carrier protein; (d) radioactive acyl thioester substrate; and (e) Scintillation Proximity Assay (SPA) support system, where the SPA support system is coated with receptors having high affinity for the ligand moiety of the conjugate; and measuring the radioactivity attached as a result of this specific ligand-receptor interaction.

Yet another objective of the present invention is to provide a faster more direct assay for KASIII activity. In the furtherance of this and other objectives, an assay is provided that does not require either protein precipitation or acid wash steps, or the use of polyacrylamide gels.

An additional objective of the present invention is to provide an assay that is amenable to high throughput screening.

Further objects, features and advantages of the invention will be apparent from the following detailed description taken in conjunction with the accompanying drawings.

DETAILED DESCRIPTION OF THE INVENTION

Definitions and Abbreviations

Figure 1:
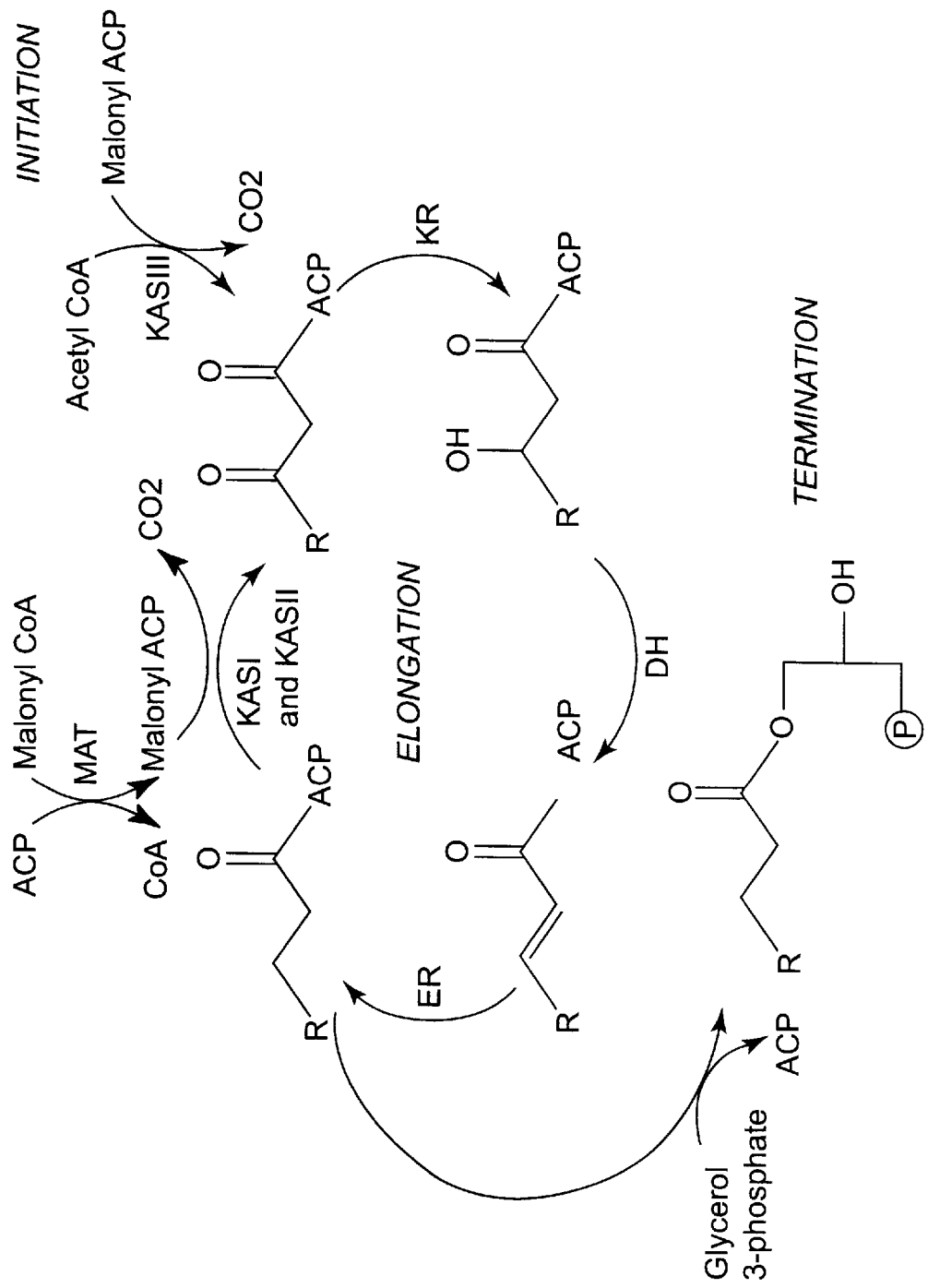
FIG. 1. Schematic representation of type II fatty acid biosynthesic pathway.

ACP: Acyl Carrier Protein
BMACP : Biotinylated Malonyl-Acyl Carrier Protein
CoA: Coenzyme A
DMSO: Dimethyl Sulfoxide
DTT : Dithiothreitol
ESI-FTICR-MS: Fourier Transformation Cyclotron Resonance Electrospray Ionization Mass Spectrometry
MACP: Malonyl-Acyl Carrier Protein
NHS-Biotin: N-Hydroxysuccinimidobiotin
PBS: Phosphate Buffered Saline
SPA: Scintillation Proximity Assay
TCA: Trichoroacetic Acid

DETAILED DESCRIPTION

The present invention provides scintillation proximity assays (SPAs) in which the activity of enzymes involved in the type II fatty acid biosynthetic pathway can be rapidly and efficiently determined. The assays are thus amenable to use in, for example, high throughput screening methods. SPA technology uses a support system (e.g. a bead) in which scintillant is trapped or impregnated within the support system. The support system further comprises high affinity receptor molecules immobilized on or near its surface such that the receptors are accessible to suitable ligands. Scintillation occurs when a weak energy radioactive isotope, such as $^3H$, is brought sufficiently close to the SPA support system. This can occur, for example, through binding of a ligand which is attached to a radiolabeled moiety such as a radiolabeled reaction product. Scintillation can then be measured directly. In the practice of the present invention, the use of SPA obviates the need for separation of a radioactive product from the radiolabeled substrate and milieu in which it is produced, thereby simplifying and speeding up assay procedures. Assays in the SPA format do not involve any cumbersome washing steps, and are therefore readily amenable to automation for high-throughput screening.

In one embodiment of the present invention, the SPA support system is a bead which has been impregnated with scintillant and which has immobilized high affinity receptor molecules located on the surface of the bead. Such beads are known to those of skill in the art and are commercially available, for example, from Amersham. However, those of skill in the art will recognize that other arrangements of such a support system can also be employed in the practice of the present invention. For example, the scintillant may be trapped in a horizontal surface (e.g. in the wells of a microtiter plate), in a fiber, in "spots" or "lanes" on a surface, and the like. Further, the support system may be composed of any material which is capable of trapping scintillant. Any appropriate shape, configuration or composition of support system may be utilized in the practice of the present invention, so long as the support system contains: accessible receptors for binding a suitable ligand, and trapped scintillant.

By "ligand" we mean a moiety that serves to tether a radioactive reaction product to the SPA support system by binding to the receptor located thereon. The ligand is ultimately attached to the radioactive product, and the radioactive product is thus "tagged" by the ligand. In the practice of the present invention, the ligand is initially attached (covalently, ionically, or by other means) to the acyl carrier protein substrate (which may be either ACP or MACP, depending on the enzyme or activity that is being assayed) and becomes incorporated into the enzyme reaction product. In one embodiment of the present invention, the ligand is biotin. However, those of skill in the art will recognize that other suitable moieties exist that can be used as ligands in the practice of the present invention. For example, antibodies, polyhistidine tags, and the like may be utilized.

Further, the ACP or MACP may be synthesized as a chimeric protein with a binding protein (for example, maltose binding protein) such that the binding protein portion of the chimera functions as a component of the "ligand-receptor" interaction. Any moiety which can be attached to the ACP or MACP substrate without interfering with that substrate's ability to be acted upon by the enzyme being assayed may be utilized in the practice of the present invention.

The reaction products detected by the practice of the present invention are radiolabeled. The radiolabel in the product is derived from a radiolabeled substrate (e.g. a radiolabeled thioester) which becomes incorporated into the product by the action of the enzyme. In a preferred embodiment of the present invention, the radiolabel is tritium. However, those of skill in the art will recognize that other suitable radioactive isotopes exist which can also be utilized in the practice of the present invention, for example, $^{14}C$. Any isotope which causes the scintillant of the SPA support system to emit an increase in signal upon ligand binding may be utilized in the practice of the present invention.

The present invention employs "SPA support systems" which have attached thereto accessible receptor molecules. By "accessible", we mean that the receptor molecules are positioned on the support system in such a manner that ligands for which they have an affinity are able to contact the receptors and bind to the receptors.

With respect to the receptors themselves, in a preferred embodiment of the present invention, the receptor is avidin or streptavidin, which has a high affinity for the ligand biotin. However, those of skill in the art will recognize that many appropriate affinity receptors exist which can be utilized in the practice of the present invention. For example, if the ligand is a histidine tag, an appropriate interaction can be obtained using immobilized divalent cations such as nickel or cobalt. If the ligand is a binding protein (e.g. maltose binding protein, i.e. the ACP or MACP has been synthesized as a chimera as described above) then an interaction could be obtained using an appropriate immobilized binding moiety such as maltose. Further, antibodies may be utilized as receptors. Any suitable receptor may be immobilized on the support system, so long as the receptor has an appropriate affinity for the ligand which has been used to tag the radioactive product being generated by the action of the enzyme that is being assayed.

Further, those of skill in the art will recognize the that terms "ligand" and "receptor" are relative in that a moiety that is a ligand in one system may be the moiety that is considered a "receptor" in another system. For the purposes of this application, "ligand" refers to the binding moiety that is attached to the product that is being detected, and "receptor" refers to the binding moiety that is attached to the SPA support system and that binds such a ligand.

Figure 2:
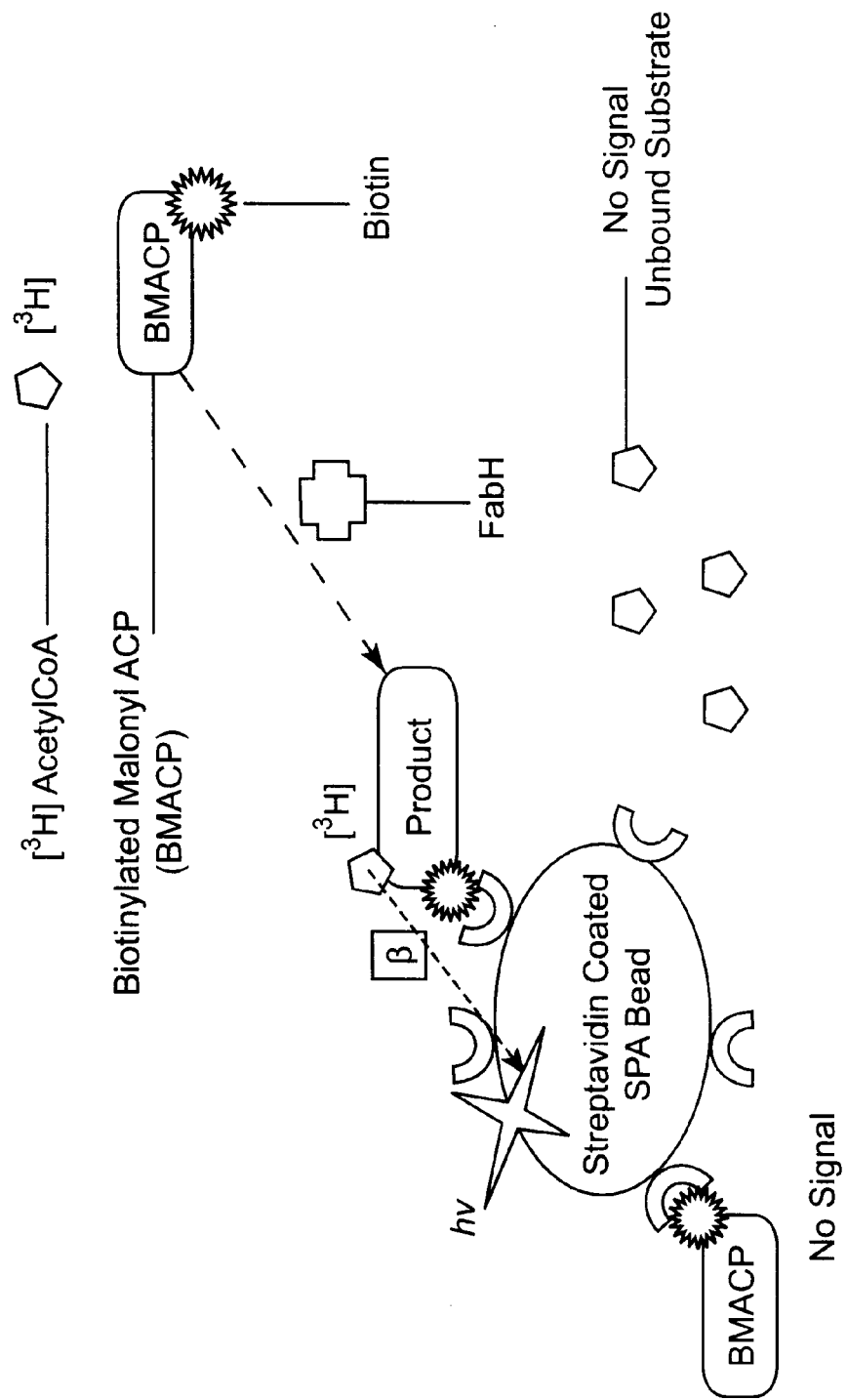
FIG. 2. Schematic representation of the scintillation proximity assay for KAS III.

A schematic representation of a scintillation proximity assay (SPA) for KASIII is illustrated in FIG. 2. In this assay, KASIII catalyzes the condensation of radioactive acyl-CoA (acetyl-CoA in this case) and biotinylated malonyl-ACP (BMACP), generating radiolabeled biotinylated acetoacetyl-ACP. Once the streptavidin-coated SPA beads are added to the reaction mixture, this $^3H$ labeled biotinylated product is captured by the streptavidin-coated SPA beads as a result of the specific biotin/streptavidin binding. The radiolabeled product is thus brought into proximity of the scintillant impregnated within the bead. Such proximity results in a light emission readily detectable in, for example, a microtiter plate scintillation counter. The unreacted $^3H$ acetyl-CoA substrate remains in solution and is sufficiently distant from the scintillant that no significant signal is observed. The SPA technology in this application therefore enables KASIII assays to be carried out without the requirement for a separation step, and hence, provides a novel assay method more readily amenable for automated high-throughput screening than the current KASII assay.

The assay methods of the present invention are carried out by combining the requisite components into a reaction mixture under suitable reaction conditions. By "suitable reaction conditions" we mean conditions of pH, ionic strength, and the like which are hospitable to the enzyme and various reactants in the reaction mixture. Specific embodiments of such conditions are given in the Examples section below. In general, the reaction mixture will comprise the enzyme that is being assayed, a radiolabeled substrate, and a substrate that is tagged with a ligand. After allowing the components to react for an appropriate length of time, the reaction mixture is contacted with a SPA support system under conditions which allow binding of ligand and receptor and any resulting scintillation signal is detected. Those of skill in the art will recognize that many methods are available for the detection and quantitation of scintillation.

In one embodiment of the present invention, the enzyme to be assayed is KASIII. However, those of skill in the art will recognize that the assay and methods of the present invention can be readily adapted to the analysis of other enzymes involved in the type II fatty acid biosynthetic pathway; reference to KASII is for convenience only and should not be construed as limiting.

In order to fully appreciate the scope of the application of the methods of the present invention, it is useful to describe the relevant enzymatic activities which can be carried out by the FAS II enzymes. Those activities fall into the following three categories:

1. Malonyl Transferase Activity: This term describes the transfer of a malonyl group. In the case of the malonyl transferase activity of MAT (also known as FabD, MCAT, MT) the malonyl group is transferred between malonyl CoA and ACP. Thus MAT catalyzes the reversible conversion of malonyl CoA and ACP to malonyl ACP and CoA. MAT plays a critical role in fatty acid biosynthesis, providing the malonyl ACP extender unit used in all KAS-catalyzed condensation steps. The use of radiolabled malonyl CoA and a tagged ACP (e.g. biotin) would allow a SPA assay format to be used for assaying MAT activity. MAT inhibitors could represent novel therapeutic agents.

2. Ketoacyl Synthase Activity: This term describes the formation of a 3-ketoacyl thioester product. Ketoacyl synthases catalyze formation of such products by catalyzing a decarboxylative condensation between an acyl thioester and malonyl ACP. In the case of KASIII (FabH) the acyl thioester uses coenzyme A. As noted above, the nature of the acyl group varies dramatically depending upon which organism the KASIII is taken from. KASIII initiates fatty acid biosynthesis. In the case of the KASI and KASII the preferred acyl thioesters are made from the acyl carrier protein, not coenzyme A (again, the nature of the acyl group can again vary quite dramatically). The KASI and KASII enzymes are used in fatty acid chain elongation, not initiation. All of the enzymes (KASI-KASIII) can be assayed using the technology presented in the instant invention, for example, by using tagged (biotin) malonyl ACP and the appropriate radiolabeled acyl thioester.

3. Acyl Transferase Activity: This term describes the transfer of an acyl group. For the purposes of this patent it refers to the demonstrated ability of ketoacyl synthases to catalyze acyl transfer between two different thioesters. In the case of KASIII, this activity catalyzes the reversible conversion of acyl CoA and ACP to acyl ACP and CoA. Thus, this enzyme activity can be assayed with an SPA format using a radiolabeled acyl CoA and a tagged (e.g. biotin) ACP. The acyl transferase activity of the KASI and KASII could catalyze transfer of a radiolabeled acyl group from acyl ACP to a tagged (e.g. biotin) ACP. Therefore, this activity could also be followed using a SPA format. Acyl transferase activity is known to be less efficient than the corresponding ketoacyl synthase activity of these enzymes. However, a potential advantage in assaying this activity is that it is easier to make the tagged ACP substrate (as compared to making tagged malonyl ACP).

The present invention provides methods for assaying enzyme activities which include but are not limited to: malonyl transferase activity, ketoacyl synthase activity, and acyl transferase activity.

FAS II enzymes which are amenable to assay by the methods of the present invention include KASI, KASII, KASIII and MAT. Those of skill in the art will recognize that any FAS II enzyme for which two suitable substrates can be generated, one of which is a radiolabeled and one of which is tagged with a ligand such that the product of a reaction between the two substrates is both radiolabeled and tagged with the ligand may be assayed by the methods of the present invention.

In other words, while the efficacy of the assay has been demonstrated for KASIII, it can also be extended for screening for KASI, KASII, and MAT modulators. MAT converts malonyl CoA to malonyl ACP. Malonyl ACP is the substrate used by all keto acyl ACP synthases (including KASIII). Compounds which specifically modulate MAT, like those that inhibit a KAS, represent potential leads for the generation of new antimicrobial and antiparastic therapeutic agents. Currently MAT assays, like KASIII assays, are conducted using a TCA-precipitation. This method utilizes radiolabeled malonyl CoA and ACP as substrates. MAT catalyzes formation of radiolabeled malonyl ACP which can be TCA-precipitated and washed, and therefore separated from the radiolabeled malonyl CoA. A SPA format, in accordance with the present invention, would use radiolabeled malonyl CoA and then an appropriately tagged acyl carrier protein (for instance biotin). The biotinylated malonyl ACP could then be captured on the SPA beads and counted directly. An exemplary embodiment of the assay, in accordance with the present invention, provides a biotinylated ACP that works as a substrate in the acyl/acetyl transacylase activity of KASIII (this transacylase activity is a side activity of the condensing/ketoacyl ACP synthase activity of this enzyme). Therefore the same substrate could be used for malonyl transacylase activities. It is well established, (Zhou, P., Florova, G., and Reynolds, K. A. 1999. Chem. Biolog., 6: 1–8), and incorporated herein by this reference, that the MAT enzyme is at least as tolerant of different ACPs as the KASIII.

With respect to the radiolabeled substrates which are utilized in the pracice of the present invention, those of skill in the art will recognize that the radiolabeled substrate that is selected for use will depend on many factors, including the nature and origin of the enzyme that is being assayed, availability of and cost of the substrate, stability of the substrate, and the like. For example, when KASIII is being assayed, in one embodiment of the present invention the radiolabeled substrate is acetyl CoA. However, other radiolabeled thioesters may also be used to assay KASII and the other FAS II enzymes. The thioester may be but is not restricted to Coenzyme A, and ACP. The acyl group may be, but is not restricted to, butyryl, isobutyryl, or myristoyl. The exact nature of the acyl group of choice may vary and any radiolabeled thioester which produces a radiolabeled FASII enzyme product that can be detected by the method of the present invention may be used in the practice of the present invention.

The present invention provides a Scintillation Proximity Assay which can be utilized for assessing the activity of FAS II enzymes in a rapid and efficient manner. Thus, the assay is amenable to high-throughput screening methodology and would be useful in identifying substances which modulate the activity of FAS II enzymes. In a preferred embodiment of the present invention, such substances are inhibitors of the FAS II enzymes. However, those of skill in the art will recognize that the present invention may be utilized to screen compounds for any purpose, such as to identify compounds which enhance enzyme activity.

In some embodiments of the present invention, the FAS II enzymes which are assayed are derived from bacteria, e.g. KAS III from *Streptomyces glaucesecens* and *Escherichia coli* as described in the Examples section. However, those of skill in the art will recognize that FAS II enzymes from any source may be assayed by the methods of the present invention. For example, FAS II enzymes from plants may be assayed via SPA. The methods of the present invention may thus be useful for identifying compounds which are useful as herbicides in that they inhibit FAS II enzymes in plants. Conversely, compounds which enhance the activity of FAS II enzymes in plants may be useful for increasing the production of selected fatty acids in plants. The methods of the present invention may be utilized to assay FAS II enzymes from any source, including native and recombinant or otherwise modified (e.g. proteolytically or chemically modified) FAS II enzymes, and the assay may be conducted for any purpose.

The present invention also provides new compositions of matter. The new compositions of matter are biotinylated acyl carrier protein and biotinylated malonyl acyl carrier protein. Details of how to make these compounds are given in the Examples section.

The following Examples are given to illustrate various embodiments of the present invention but should in no way be construed to limit the instant invention in any way.

EXAMPLES

MATERIALS AND METHODS

Sources of Compounds

The following reagents were used: NHS-biotin (Pierce); Acyl carrier protein (*E. coli*), Imidazole, DMSO and Malonyl-CoA (Sigma); DTT (Fisher scientific); [$^3$H] Acetyl-CoA (specific activity 20 Ci/mmol) (Moravek); Iodoacetamide (Aldrich); *Escherichia coli* BL21 (DE3 pLysE) (Novagen). Streptavidin-coated yttrium sillicate (YS) scintillation proximity fluorospheres (SPA beads) (Amersham), *Escherichia coli* His$_6$-KASIII enzyme and thiolactomycin were kindly provided by Pfizer Inc. The *E. coli* His$_6$-KASIII protein was purified as previously described. (Heath and Rock 1995. *J Biol. Chem.* 270, 26598–26542)

Preparation of Streptomyces glaucescens KASIII and Malonyl-CoA:ACP Transacylase (MAT)

The *S. glaucescens* His$_6$-KASIII fusion protein was expressed in *Escherichia coli* BL21 (DE3 pLysE)/pLH14, in accordance with conventional protocols. Cultures grown in Luria-Bertani medium were induced with 0.4 mM isopropyl β-D-thiogalactoside (IPTG) for 4 hrs at 30° C. Cells were harvested by centrifugation, washed twice in phosphate-buffered saline (PBS), resuspended in lysis buffer (300 mM NaCl, 50 mM $Na_2HPO_4/NaH_2PO_4$, 1% Triton X-100) and lysed by high pressure homogenization (12,000–15,000 psi). The resulting cell extract was centrifuged and the supernatant was incubated with nickel-nitrilotriacetic acid agarose (Qiagen) for 30 minutes at 4° C. The resin was then washed twice with 10 volumes of 300 mM NaCl, 50 mM $Na_2HPO_4/NaH_2PO_4$, supplemented first with 20 mM then 40 mM imidazole. The KASIII was eluted with 200 mM imidazole. KASIII-containing fractions were pooled and desalted using a sephadex G-10 column equilibrated with 100 mM imidazole (pH 7.0). The KASIII solution was then dialyzed against 50% glycerol buffer (50% glycerol, 100 mM imidazole-HCl pH 7.0, 1 mM DTT), aliquoted and stored at −80° C. Quantitation of protein was carried out using dotmetric Protein assay kit (Bioworld). S. glaucescens $His_6$-FabD was expressed and purified from E. coli strain BL21 (DE3)/pLH16 as described previously (Han et al. 1998. J Bacteriol. 180, 4481–4486.)

Preparation of Malonyl-ACP

The recombinant S. glaucescens $His_6$-FabD was used to prepare MACP. A 1 ml reaction mixture containing 100 $\mu$M Escherichia coli ACP, 430 $\mu$M malonyl-CoA, 5 mM acetyl phosphate, 40 units phosphotransacetylase, 170 $\mu$g $His_6$-FabD in 50 mM sodium phosphate (pH 7.0) was incubated at 37° C. for 2 hrs. MACP was purified using an FPLC ion-exchange column Mono Q 5/5 (Pharmacia) pre-equilibrated with 0.2 M NaCl in 50 mM Bis-Tris (pH 6.5). This column was washed with this same buffer for 30 min at 0.2 ml/min before a linear 12 ml gradient from 0.2 to 0.5 M NaCl was applied. The purity of MACP was monitored by conformationally sensitive gel electrophoresis (13% polyacrylamide, 0.5 M urea) (Choi, K. H., Heath, R. J. and Rock, C. O. 2000. β-ketoacyl-acyl carrier protein synthase III (FabH) is a determining factor in branched-chain fatty acid biosynthesis. J Bacteriol 182: 365–70). MACP-containing fractions were pooled, concentrated and desalted by three cycles of centrifugation with distilled water using Microcon 3 microconcentrator (Amicon). The MACP solution was then stored in aliquots at −80° C. until required. The molecular weight of MACP was determined by Fourier transformation cyclotron resonance electrospray ionization mass spectrometry (ESI-FTICR-MS). Quantitation of MACP was carried out using dotmetric protein assay kit (Bioworld).

Biotinylation of Malonyl-ACP

Malonyl-ACP was biotinylated by treating with NHS-biotin (Pierce). A 120 $\mu$l 100 mM PBS (pH 8.0) solution containing MACP (185 $\mu$M) and NHS-biotin (1.85 mM final concentration from a 60 mM stock solution in DMSO) was incubated at 23° C. for 2 h. Biotinylated malonyl-ACP (BMACP) was separated from unreacted NHS-biotin by three cycles of centrifugation and washing steps using Microcon 3 microconcentrator (Amicon). The BMACP was stored in aliquots at −80° C. until required and was stable for at least three months under such condition. The concentration of biotinylated malonyl-ACP (BMACP) was determined using dotmetric protein assay kit (Bioworld). An average of four biotin molecules were shown to be incorporated per MACP molecule by this procedure (Immunopure HABA kit, Pierce). The biotinylation of ACP was carried out in an analogous manner.

SPA Beads Stock Solution

SPA beads (available from Amersham) were suspended in PBS 20% glycerol to a concentration of 10 mg/ml. This stock solution was stored at 4° C. for as long as 1 month. A typical assay used 50 $\mu$l of this solution which contains 0.5 mg of SPA beads with a biotin binding capacity of at least 140 pmol.

KAS III Assays and Inhibition Studies

The standard reaction mixture contained the following components in a final volume of 20 $\mu$: S. glaucescens $His_6$-KASIII 0.9 kg, 100 mM imidazole, pH 7.0, 2.6 $\mu$M BMACP (MACP), [$^3$H] acetyl-CoA 0.6 $\mu$M (0.24 $\mu$Ci, specific activity 20 Ci/mmol). The reaction was initiated by adding [$^3$H] acetyl-CoA and incubated at 30 ° C. for 10 minutes.

For the KASIII SPA, the reaction was terminated by the sequential addition of 100 $\mu$l of 100% ethanol (which denatures the KASIII) and 50 $\mu$l of the SPA bead solution (10 mg/ml). The mixture was then incubated for 2 hr at 23° C. with gentle shaking. After allowing the beads to settle the sealed OptiPlate (Packard, Meriden, Conn.) was counted using a TopCount (Packard) set up in SPA mode. A background signal was obtained by carrying out the assay in absence of KASIII. This background signal was subtracted from KASIII SPA signals.

In the KASIII TCA precipitation assay, the reaction was quenched by the addition of 200 $\mu$l ice cold 10% TCA, incubated on ice for 10 min and centrifuged at 13,000 g for 10 min. The supernatant was discarded and the pellet was resuspended with another 200 $\mu$l of cold TCA and centrifuged. The pellet bound $^3$H labeled product was dissolved in 2% SDS, 20 mM NaOH and quantitated by liquid scintillation counting. The Escherichia coli KASIII assay was performed in the same manner except that the incubation time was reduced to 2 minutes, and 0.13 $\mu$g of protein and 0.4 $\mu$M MACP (BMACP) were used in the assay.

In all inhibitor studies, the inhibitor was first dissolved in DMSO and preincubated with enzyme for 15 minutes at 23° C., prior to addition of substrate. The final DMSO concentration in each of these assays remained below 1%.

Kinetic Determinations for MACP and BMACP

The apparent Km for MACP with the S. glaucescens KASIII was determined using the standard TCA precipitation assay with the following modifications: tritiated acetyl-CoA at a final concentration of 13.3 $\mu$M (0.4 $\mu$Ci, specific activity 1 Ci/mmol ) was incubated at 30° C. for 5 min with various concentrations of MACP (0.39–18.7 $\mu$M) in a volume of 30 $\mu$l. The apparent $K_m$ for BMACP with the S. glaucescens KASIII was determined in SPA format. Tritiated acetyl-CoA at a final concentration of 7.5 $\mu$M (0.6 $\mu$Ci, specific activity 4 Ci/mmol) was incubated at 30° C. for 9 min with various BMACP concentrations (0.28 to 9 $\mu$M).

EXAMPLE 1

Preparation of MACP and BMACP

Figure 3:
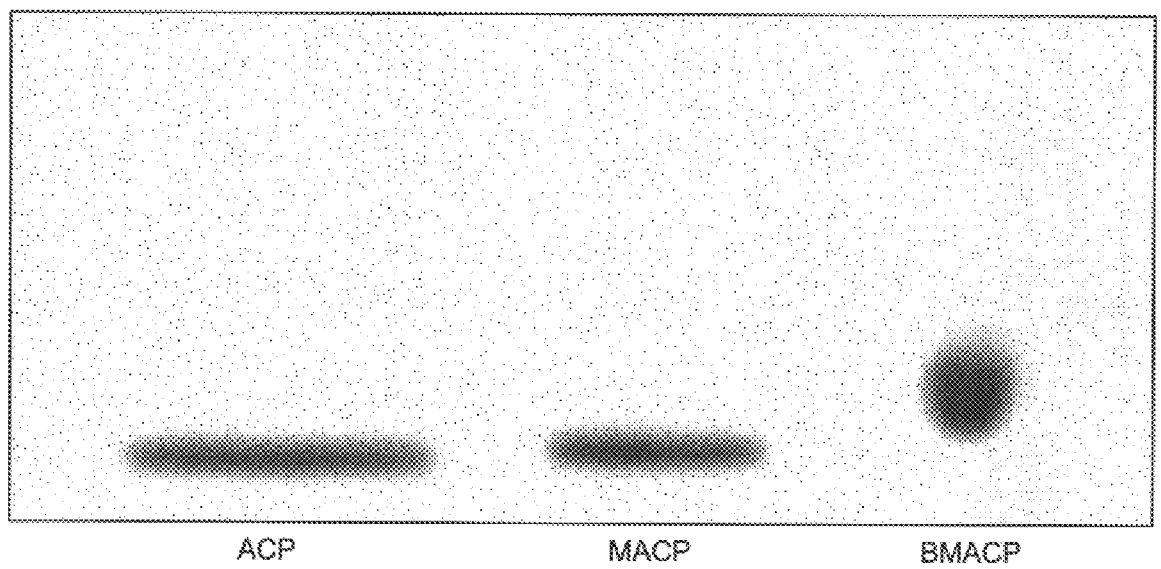
FIG. 3. Conformationally sensitive gel analyses of ACP, MACP and BMACP. Samples were subjected to electrophoresis in a 13% acrylamide gel containing 0.5 m urea at a constant current of 23 mA.

The MACP substrate for a KASIII TCA precipitation assay was generated following a standard protocol from Escherichia coli ACP and malonyl-CoA using the S. glaucescens $His_6$-FabD. The addition of acetylphosphate and phosphotransacetylase in this assay convert the coenzyme A byproduct of the first reaction to acetyl-CoA, thus shifting the equilibrium towards the desired product MACP. MACP was purified by ion exchange chromatography and shown by conformationally-sensitive gel electrophoresis to be resolved from ACP (FIG. 3). The average experimental molecular weight ($M_r$) of MACP was determined to be 8935.8±0.4 Da using ESI-FTICR-MS which is in good agreement with the theoretical calculation for MACP (estimated average $M_r$ for Escherichia coli holo-ACP is 8847). The BMACP required for a KASIII SPA was then prepared by biotinylation of MACP using NHS-biotin. Analysis by conformationally sensitive gel electrophoresis indicated that the BMACP and MACP had similar levels of purity (FIG. 3). A comparison of the BMACP and MACP as substrates for the *S. glaucescens* KASIII in standard TCA precipitation assays was carried out. Under all conditions tested, the same concentrations of the two substrates resulted in the formation of similar levels of radiolabeled product. This observation suggested that BMACP is a comparable substrate to MACP and could be used to develop a SPA for KASIII. Similar activities were also observed for ACP and biotinylated ACP used in an acyl transferase assay of KASIII.

EXAMPLE 2

Development of a SPA for KASIII

Figure 4A:
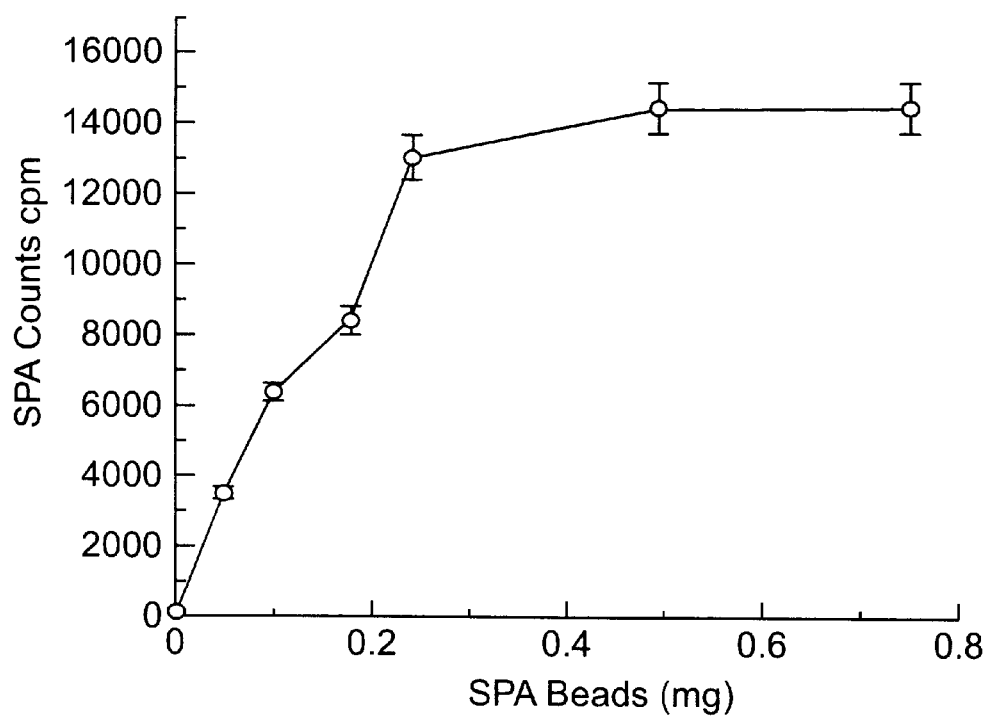
FIG. 4. (A) Dependence of SPA signal on bead concentration using the *Streptomyces glaucescens* KASIII. (B) Effect of *S. glaucescens* KASIII concentration on SPA signal. The straight line is a least-squares fit to the data. All data points are expressed as the average of duplicates.

The typical KASIII SPA consisted of incubating BMACP, radiolabeled acetyl-CoA, and KASIII for a specified time. The reaction was terminated and the assay components were combined with SPA beads for product quantitation. In this assay both the radiolabeled product and the unreacted unlabeled BMACP substrate can bind to the beads. Theoretically a maximal SPA signal will be achieved when the biotin binding capacity of the SPA beads exceeds the amount of BMACP (52 pmol) used in a standard assay. This prediction was verified by determining the relationship between SPA signal and the SPA bead quantity (FIG. 4A). In assays with the *S. glaucescens* KASIII, a maximal SPA signal was obtained with bead quantities of 0.5 mg (140 pmol biotin binding capacity). In contrast, SPA assays conducted with bead quantities less than 0.25 mg (70 pmol binding capacity) resulted in significant reductions in the SPA signal (FIG. 4A), indicative of incomplete binding of the radiolabeled product.

Figure 4B:
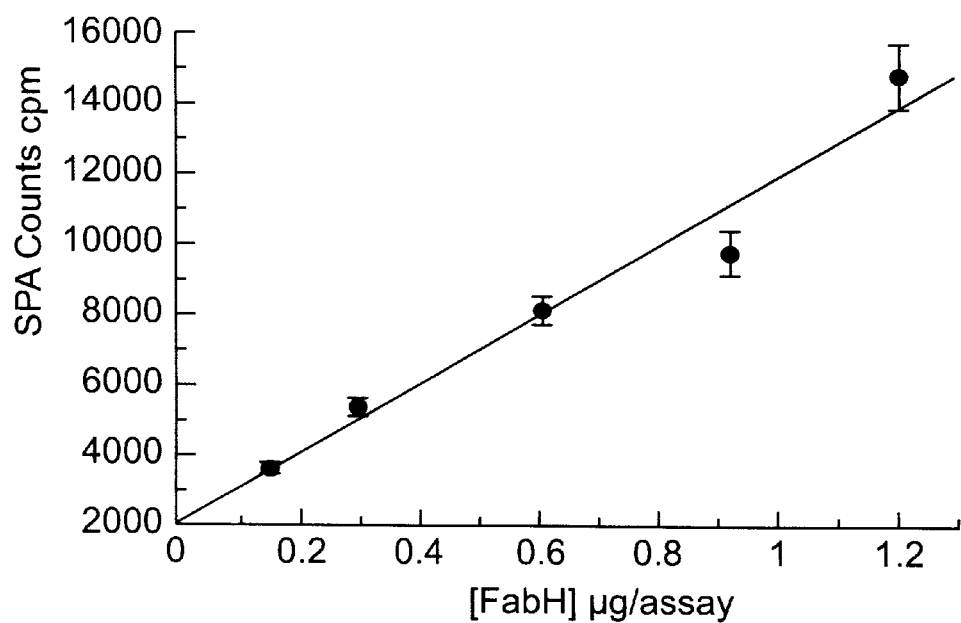

Another variable investigated in the SPA development was the quantity of the *S. glaucescens* KASIII used. As shown in FIG. 4B, a linear relationship was observed between product formation (as determined by the SPA signal) and enzyme concentration over a 0–1.2 $\mu$g/assay range. The standard assay uses 0.9 $\mu$g *S. glaucescens* KASIII which minimizes the amount of enzyme while maintaining a signal to background ratio greater than 10:1. Assays carried out with the *E. coli* KASIII used 0.13 $\mu$g of protein assay.

Figure 5:
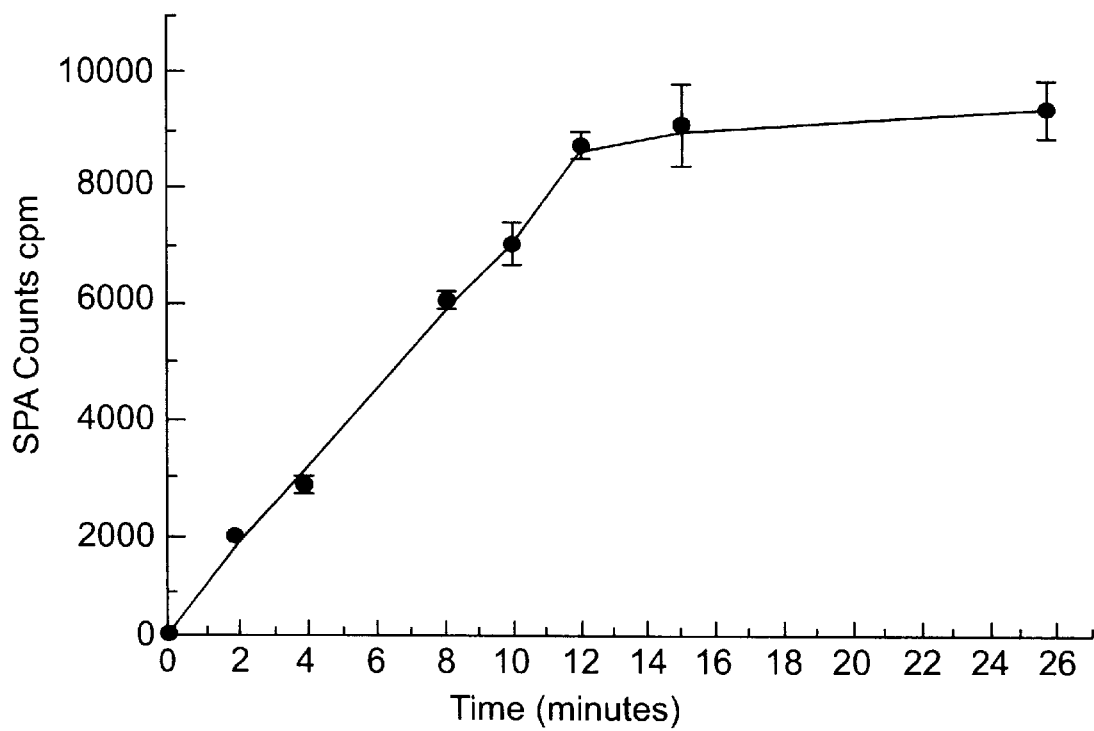
FIG. 5. Time course of tritiated acetoacetyl-ACP formation in the *S. glaucescens* KASIII SPA. All data points are expressed as the average of duplicates.

The time course of product formation was evaluated over 25 min using the 0.9 $\mu$g S. glaucescens KASIII in a standard SPA (FIG. 5). The reaction proceeded in an apparent linear fashion for the first 12 minutes of the incubation. An incubation time of 10 min produced approximately 75% of the maximal signal and was chosen for a routine SPA.

Figure 6A:
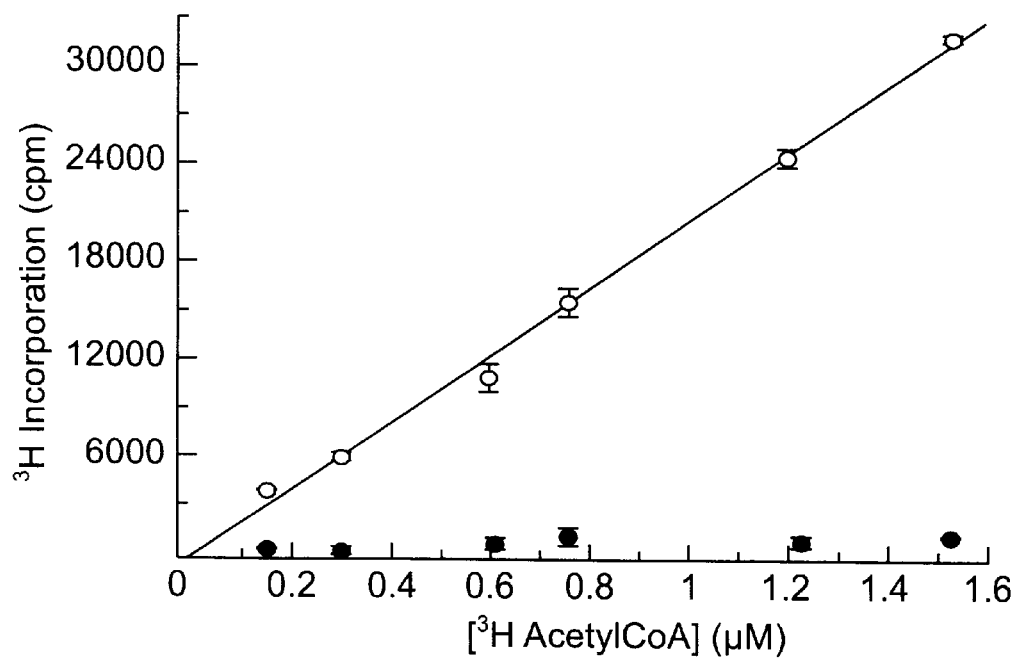
FIG. 6. (A) Effect of acetyl-CoA concentration on SPA signal in assays with *S. glaucescens* KASIII (open circles). Assays carried out in the absence of KASIII and BMACP are shown (closed circles). Reactions were performed with the indicated acetyl-CoA concentrations (specific activity 20 Ci/mmol). (B) Effect of BMACP concentration on SPA signal in assays with *S. glaucescens* KASIII. All data points are expressed as the average of duplicates.
Figure 6B:
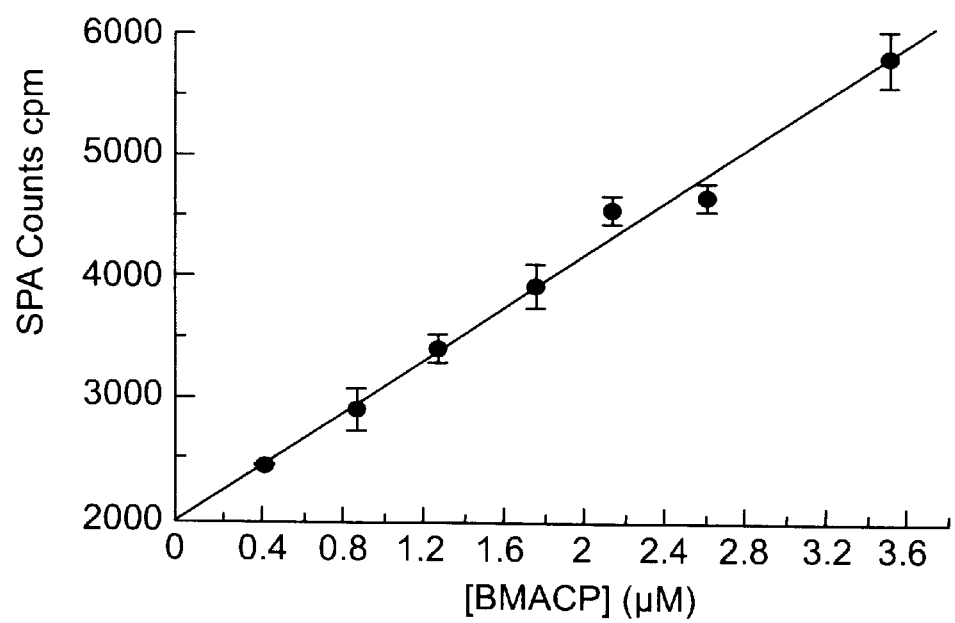

The effect of both the radiolabeled acetyl-CoA and BMACP substrates on the KASIII SPA was also evaluated. In the case of acetyl-CoA, a linear relationship was observed between substrate concentration (0–1.6 $\mu$M) and the SPA signal (FIG. 6A), suggesting that the $K_m$ of the *S. glaucescens* KASIII for acetyl-CoA is greater than 1.6 $\mu$M. Previous analyses of this enzyme using a TCA-precipitation assay have determined a $K_m$ value of 3.0 $\mu$M. A linear relationship was also observed between BMACP concentration (0–3.6 $\mu$M) and the SPA signal (FIG. 6B), consistent with the assays being conducted at or below the BMACP $K_m$ of the *S. glaucescens* KASIII. A $K_m$ of 3.7 $\mu$M has previously been determined using a TCA precipitation assay. A concentration of 2.6 $\mu$M BMACP and 0.6 $\mu$M acetyl-CoA (0.2 $\mu$Ci, specific activity 20 Ci/mmol) were selected for the KASIII SPA. These non-saturating substrate concentrations allow competitive KASIII inhibitors to be readily detected in a SPA, and minimize the amount of the two substrates used in an assay while maintaining a signal to noise ratio greater than 10:1.

The tolerance of the KASIII SPA to dimethylsulfoxide (DMSO), a solvent typically used to dissolve inhibitors in high throughput screens, was also determined. This analysis revealed that there was no significant decrease in the SPA signal at DMSO concentrations below 1.5% v/v and approximately a 50% reduction in the SPA signal with DMSO concentration of 10% v/v. Inhibition studies on KASIII using the SPA were conducted with final DMSO concentrations at or below 1% v/v assay to obviate the negative effect of the solvent.

These results demonstrate that a SPA assay can be used to detect KASIII activity in an efficient and sensitive manner.

EXAMPLE 3

Comparison of the KASIII SPA and TCA Precipitation Assay

Figure 7A:
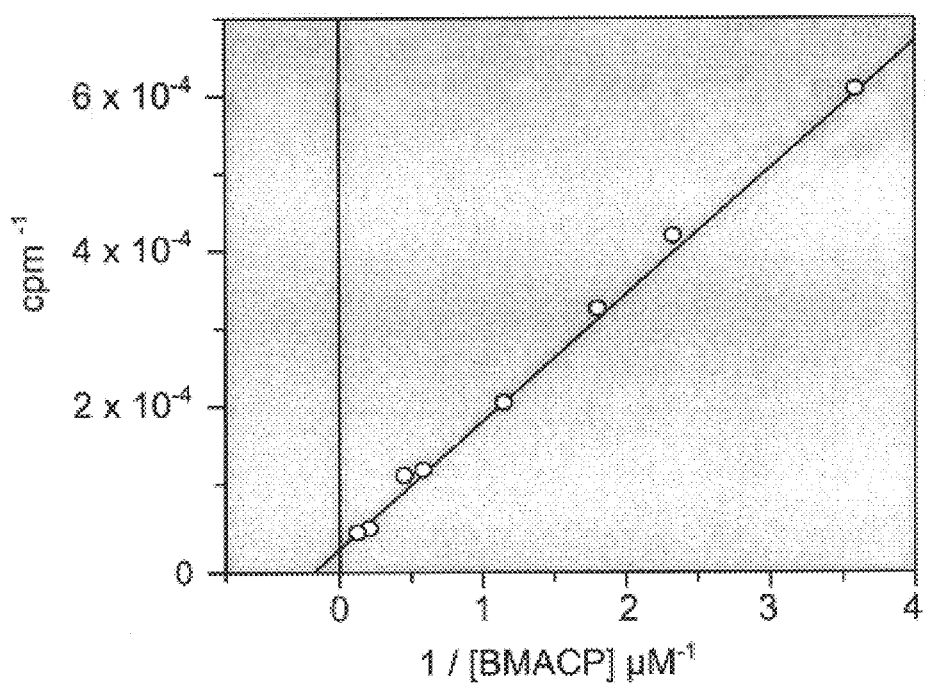
FIG. 7. Lineweaver-Burk plots of the relationship between BMACP (A) and MACP (B) and S. glaucescens KASIII activity using the SPA and TCA-precipitation assay, respectively. Apparent Km values for the two substrates were determined and are reported in the text.
Figure 7B:
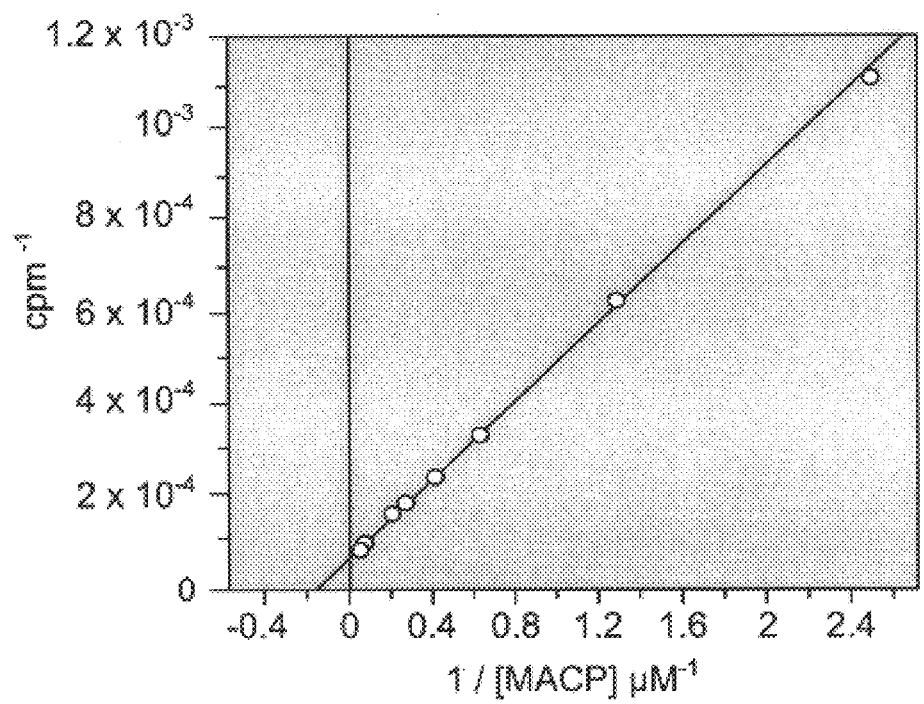
Figure 8A:
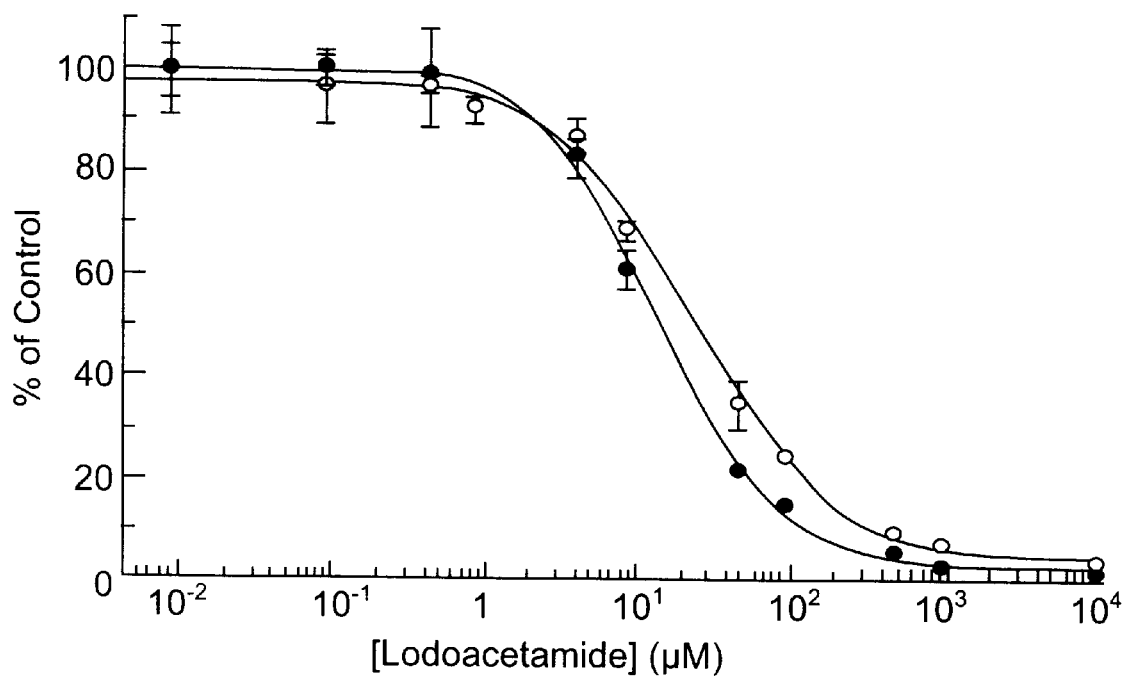
FIG. 8. KASIII inhibition studies. The inhibitory effect of iodoacetamide (A) and thiolactomycin (B) on the *S. glaucescens* KASIII and *E. coli* KASIII, respectively. Studies were carried out using both the TCA precipitation assay (open circles) and SPA (closed circles) format. The same concentration of acetyl-CoA was used in both assays. A background signal obtained in the absence of KASIII was subtracted and the data are represented as a percentage of the signal obtained in the absence of the inhibitor. Each data point is the average of two determinations.
Figure 8B:
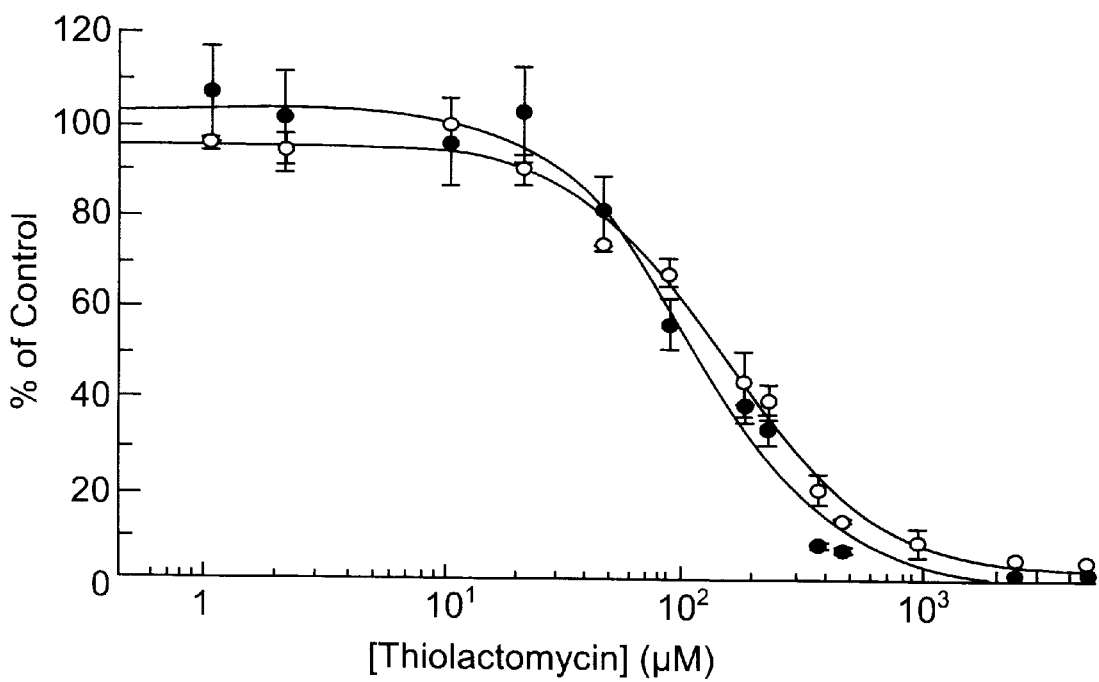

A series of kinetic and inhibition studies were carried out in order to compare the KASIII SPA with the TCA precipitation assay. A $K_m$ value of 7.2±2.6 $\mu$M was determined for the BMACP substrate using *S. glaucescens* KASIII in SPA format (FIG. 7A). A simultaneous set of experiments using the traditional TCA-based assay determined a $K_m$ of 6.1±0.4 $\mu$M for MACP (FIG. 7B The two assays were also used with the *S. glaucescens* $His_6$-KASIII to determine the effect of iodoacetamide, which modifies the active site cysteine residue essential for forming the acyl enzyme intermediate (FIG. 8A). An $IC_{50}$ of 25±3 $\mu$M was determined for iodoacetamide in the TCA precipitation assay, compared with a value of 15±1 $\mu$M determined in the SPA. Likewise, the effect of thiolactomycin, a known KASIII inhibitor, on the *E. coli* KASIII was assessed using the two different assays (FIG. 8B). An $IC_{50}$ of 124.4±14 $\mu$M and 160±14 $\mu$M were obtained for the SPA and TCA precipitation assays, respectively. These $IC_{50}$ values are higher than the concentrations of thiolactomycin required for inhibition of the *E. coli* KASIII. The in vitro effectiveness of KASIII inhibition by thiolactomycin, however, has previously been shown to be variable and highly dependent upon the assay conditions.

These results both confirm that BMACP is an effective substrate for KASIII and comparable to MACP. The results also demonstrate that the SPA technology can be applied for carrying out kinetic assays with KASIII. Finally, these results demonstrate that KASIII inhibition by inhibitors (such as, but not restricted to, thiolactomycin) can be detected and appears to function equally well in the HTS-adaptable SPA format as in other more cumbersome assay formats.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A method to assay an enzymatic activity of a type II fatty acid biosynthetic enzyme, comprising the steps of:

forming a reaction mixture under suitable reaction conditions by combining
  a) said type II fatty acid biosynthetic enzyme;
  b) a tagged substrate which has been tagged with a ligand, wherein said substrate is ACP or MACP; and
  c) a radiolabeled acyl or malonyl thioester exposing said reaction mixture to a Scintillation Proximity Assay (SPA) support system, wherein said SPA support system comprises trapped scintillant and a receptor for said ligand; and measuring a level of scintillation that correlates with a level of activity of said enzyme.

2. The method of claim 1 wherein said type II fatty acid biosynthetic enzyme is selected from the group consisting of: KASI, KASII, KASIII, and MAT.

3. The method of claim 1 wherein said ligand is biotin.

4. The method of claim 1 wherein said receptor is avidin or streptavidin.

5. The method of claim 1 wherein said radiolabeled thioester is malonyl CoA.

6. The method of claim 1 wherein said radiolabeled thioester is acetyl CoA.

7. The method of claim 1 wherein said SPA support system is selected from the group consisting of a bead and a plate.

8. A method for assessing a compound's ability to modulate the enzymatic activity of a type II fatty acid biosynthetic enzyme, comprising the steps of:
   generating a test reaction mixture and a control reaction mixture, wherein said test reaction mixture comprises
      a) said type II fatty acid biosynthetic enzyme;
      b) a tagged substrate which has been tagged with a ligand, wherein said substrate is ACP or MACP;
      c) a radiolabeled acyl or malonyl thioester
      d) said compound,
   and wherein said control reaction mixture comprises
      a) said type II fatty acid biosynthetic enzyme;
      b) a tagged substrate which has been tagged with a ligand, wherein said substrate is ACP or MACP; and
      c) a radiolabeled acyl or malonyl thioester
   exposing said test reaction mixture and said control reaction mixture to a SPA support system, wherein said SPA support system comprises trapped scintillant and a receptor for said ligand, wherein said step of exposing is carried out under conditions which allow said ligand and said receptor to bind;
   measuring a first and a second level of scintillation which respectively corresponds to said test reaction mixture and said control reaction mixture
   determining a difference between said first and second levels of scintillation, wherein said difference is correlated to said ability of said compound to modulate said enzymatic activity of said type II fatty acid biosynthetic enzyme.

9. The method of claim 8 wherein said type II fatty acid biosynthetic enzyme is selected from the group consisting of: KASI, KASII, KASIII, and MAT.

10. The method of claim 8 wherein said ligand is biotin.

11. The method of claim 8 wherein said receptor is avidin or streptavidin.

12. The method of claim 8 wherein said radiolabeled thioester is malonyl CoA.

13. The method of claim 8 wherein said radiolabeled thioester is acetyl CoA.

14. The method of claim 8 wherein said SPA support system is selected from the group consisting of a bead and a plate.

15. A kit for assaying enzymatic activity of a type II fatty acid biosynthetic enzyme, comprising
   a) a tagged substrate which has been tagged with a ligand, wherein said substrate is ACP or MACP;
   b) a radiolabeled acyl or malonyl thioester; and
   c) a SPA support system.

16. The kit of claim 15 wherein said type II fatty acid biosynthetic enzyme is selected from the group consisting of: KASI, KASII, KASIII, and MAT.

17. The kit of claim 15 wherein said ligand is biotin.

18. The kit of claim 15 wherein said receptor is avidin or streptavidin.

19. The kit of claim 15 wherein said radiolabeled thioester is malonyl CoA.

20. The kit of claim 15 wherein said radiolabeled thioester is acetyl CoA.

21. The kit of claim 15 wherein said SPA support system comprises a bead impregnated with scintillant.

22. A method for assaying ketoacyl synthase activity in an enzyme, comprising,
   forming a reaction mixture under suitable reaction conditions by combining
      a) said enzyme;
      b) malonyl acyl carrier protein, wherein said malonyl acyl carrier protein has been tagged with a ligand
      c) a radiolabeled acyl thioester
   exposing said reaction mixture to a Scintillation Proximity Assay (SPA) support system, wherein said SPA support system comprises trapped scintillant and a receptor for said ligand, and wherein said step of exposing is carried out under conditions which allow said ligand and said receptor to bind; and
   measuring a level of scintillation that correlates with a level of ketoacyl synthase activity of said enzyme.

23. The method of claim 22 wherein said enzyme is selected from the group consisting of KASI, KASII, and KASIII.

24. The method of claim 22 wherein said enzyme is KAS III and said radiolabeled acyl thioester is acetyl coenzyme A.

25. A method for assaying malonyl transferase activity in an enzyme, comprising,
   forming a reaction mixture under suitable reaction conditions by combining
      a) said enzyme;
      b) acyl carrier protein, wherein said acyl carrier protein has been tagged with a ligand; and
      c) a radiolabeled malonyl CoA;
   exposing said reaction mixture to a Scintillation Proximity Assay (SPA) support system, wherein said SPA support system comprises trapped scintillant and a receptor for said ligand, and wherein said step of exposing is carried out under conditions which allow said ligand and said receptor to bind; and
   measuring a level of scintillation that correlates with a level of malonyl transferase activity of said enzyme.

26. The method of claim 25 wherein said enzyme is MAT.

27. A method for assaying acyl transferase activity in an enzyme, comprising,
   forming a reaction mixture under suitable reaction conditions by combining
      a) said enzyme;
      b) acyl carrier protein, wherein said acyl carrier protein has been tagged with a ligand; and
      c) a radiolabeled acyl thioester;
   exposing said reaction mixture to a Scintillation Proximity Assay (SPA) support system, wherein said SPA support system comprises trapped scintillant and a receptor for said ligand, and wherein said step of exposing is carried out under conditions which allow said ligand and said receptor to bind; and
   measuring a level of scintillation that correlates with a level of acyl transferase activity of said enzyme.

28. The method of claim 27 wherein said enzyme is KAS III and said acyl donor is acyl CoA.

29. The method of claim 27 wherein said enzyme is KAS I or KAS II and said acyl thioester is acyl-ACP.

30. The method as recited in claim 22 further comprising the step of assessing a compound's ability to modulate an activity of said enzyme.

31. The method as recited in claim 25 further comprising the step of assessing a compound's ability to modulate an activity of said enzyme.

32. The method as recited in claim 27 further comprising the step of assessing a compound's ability to modulate an activity of said enzyme.

33. A method of evaluating enzymatic activity in a type II fatty acid biosynthetic pathway, said method comprising:
(a) contacting a test sample comprising a target enzyme with a test compound under suitable conditions that allow the components to interact;
(b) adding to the components a radiolabeled acyl or malonyl thioester substrate and either an acyl carrier protein or malonyl acyl carrier protein; and
(c) comparing the enzymatic activity of the target enzyme in the test sample to the enzymatic activity of the target enzyme in a sample not contacted with said test compound, wherein the difference in enzymatic activity in the test sample is indicative of the effect of said test compound on said target enzyme.

34. The method of claim 33, wherein said target enzyme comprises a KAS isozyme.

35. The method of claim 34, further comprising the step of identifying a level of inhibition.

36. The method of claim 33, wherein said test compound is a KAS isozyme inhibitor.

37. The method of claim 34, wherein said KAS isozyme is KASIII.

38. The method of claim 37, wherein said radiolabeled acyl or malonyl thioester substrate is an acyl CoA substrate.

39. The method of claim 38, wherein said acyl CoA substrate is acetyl-CoA.

40. The method of claim 34, wherein said KAS isozyme is FabD.

41. The method of claim 40, wherein the acyl carrier protein is malonyl-acyl carrier protein.

42. The method of claim 33, wherein said acyl carrier protein is biotinylated.

43. A method for identifying a test compound that modulates KAS isozyme activity, said method comprising:
contacting a test sample comprising KAS isozyme; a biotinylated malonylacyl-acyl carrier protein, and a tritiated acyl-CoA with a test compound under conditions suitable to allow the components to interact; and
comparing the KAS isozyme activity in the test sample to KAS isozyme activity in a sample not contacted with said test compound, wherein the difference in KAS isozyme activity in the test sample is indicative of the effect of said test compound.

44. An assay for measuring the activity of compounds that affect the activity of β-Ketoacyl-ACP Synthase III (KASIII) comprising, mixing the following components in solution: (a) KASIII; (b) the compound, whose effect on KASIII is to be measured; (c) conjugate comprising a high affinity moiety and an acyl carrier protein; (d) radioactive acyl thioester substrate; and (e) Scintillation Proximity Assay (SPA) support system, where the SPA support system is coated with proteins having high affinity for the affinity moiety of the conjugate; and measuring the radioactivity incorporated into the SPA support system.

45. The assay of claim 44, wherein the high affinity moiety is biotin.

46. The assay of claim 44, wherein the SPA support system is a plate.

47. The assay of claim 44, wherein the acyl carrier protein is malonyl-acyl carrier protein.

48. The rapid assay of claim 44, wherein the SPA support system is an SPA bead.

49. The rapid assay of claim 48, wherein the SPA beads are coated with avidin.

50. The rapid assay of claim 48, where the SPA beads are coated with streptoavidin.

51. The rapid assay of claim 44, where the radioactive acyl CoA substrate is acetyl-coenzyme A.

52. An assay test kit for measuring the activity of compounds that affect the activity of a KAS isozyme comprising: (a) KAS isozyme composition; (b) conjugate comprising a high affinity moiety and an acyl carrier protein; (c) radioactive acyl CoA substrate; and (d) SPA support system.

53. The assay test kit of claim 52, where the high affinity moiety is biotin.

54. The rapid assay test kit of claim 52, where the acyl carrier protein is malonyl-acyl carrier protein.

55. The rapid assay test kit of claim 52, where the radioactive acyl CoA substrate is acetyl-coenzyme A.

56. The rapid assay test kit of claim 52, where the radioactive acyl CoA substrate is acetyl-coenzyme A.

57. The rapid assay test kit of claim 52, where the SPA support system is at least one SPA bead.

58. The rapid assay test kit of claim 56, where the SPA beads are coated with avidin.

59. The rapid assay test kit of claim 56, where the SPA beads are coated with streptoavidin.

60. A rapid assay for measuring the activity of compounds that inhibit KAS from a type II fatty acid synthase comprising, mixing the following components in solution: a test compound; KAS; radiolabeled acyl thioester substrate; a tagged malonyl acyl carrier protein; a product capture element; and measuring for a signal produced when the radiolabeled acyl thioester substrate is sufficiently close to the product capture element.

61. The rapid assay of claim 60, where the radiolabeled acyl thioester substrate is acetyl CoA.

62. The rapid assay of claim 60, where the radiolabeled acyl thioester substrate is acyl carrier protein.

63. The rapid assay of claim 60, where the acyl carrier protein is tagged for KAS activity.

64. The rapid assay of claim 60, where the acyl carrier protein is tagged for transacylase activity.

65. The rapid assay of claim 60, where product capture element is at least one protein coated SPA bead.

66. The rapid assay of claim 60, where product capture element is a protein coated plate.

67. The rapid assay of claim 60, where the tagged acyl carrier protein is malonyl-acyl carrier protein.

68. The method of claim 42, wherein said biotinylated acyl carrier protein is malonylacyl-acyl carrier protein.

* * * * *